United States Patent [19]
Fein et al.

[11] Patent Number: 6,064,899
[45] Date of Patent: May 16, 2000

[54] FIBER OPTIC OXIMETER CONNECTOR WITH ELEMENT INDICATING WAVELENGTH SHIFT

[75] Inventors: Michael E. Fein, Mountain View; Willem A. Crone, Palermo, both of Calif.

[73] Assignee: Nellcor Puritan Bennett Incorporated, Pleasanton, Calif.

[21] Appl. No.: 09/065,663

[22] Filed: Apr. 23, 1998

[51] Int. Cl.[7] .................................................. A61B 5/00
[52] U.S. Cl. ...................... 600/323; 600/310; 356/41
[58] Field of Search ................................. 600/310, 322, 600/323, 325–327, 329, 331, 332, 336, 339, 341, 342, 473, 476, 478; 356/39, 41, 317, 318; 250/226, 227.16, 227.23

[56] References Cited

U.S. PATENT DOCUMENTS

| 4,684,245 | 8/1987 | Goldring | 600/332 |
| 5,303,026 | 4/1994 | Strobl et al. | 600/476 |
| 5,565,976 | 10/1996 | Fieggen et al. | 600/478 |

*Primary Examiner*—Eric F. Winakur
*Attorney, Agent, or Firm*—Townsend and Townsend and Crew LLP

[57] ABSTRACT

An oximeter probe segment with a first fiber optic for carrying light to a patient, and a second fiber optic for carrying return light from the patient. The light is of a wavelength spectrum which can be shifted by travelling through the first and second fiber optics. The probe segment includes an element which is configured to provide a signal corresponding to the shift of the wavelength spectrum through the first and second fiber optics. This signal can either be used to actually measure the shift, or the signal can itself be a coded value corresponding to the shift.

20 Claims, 9 Drawing Sheets

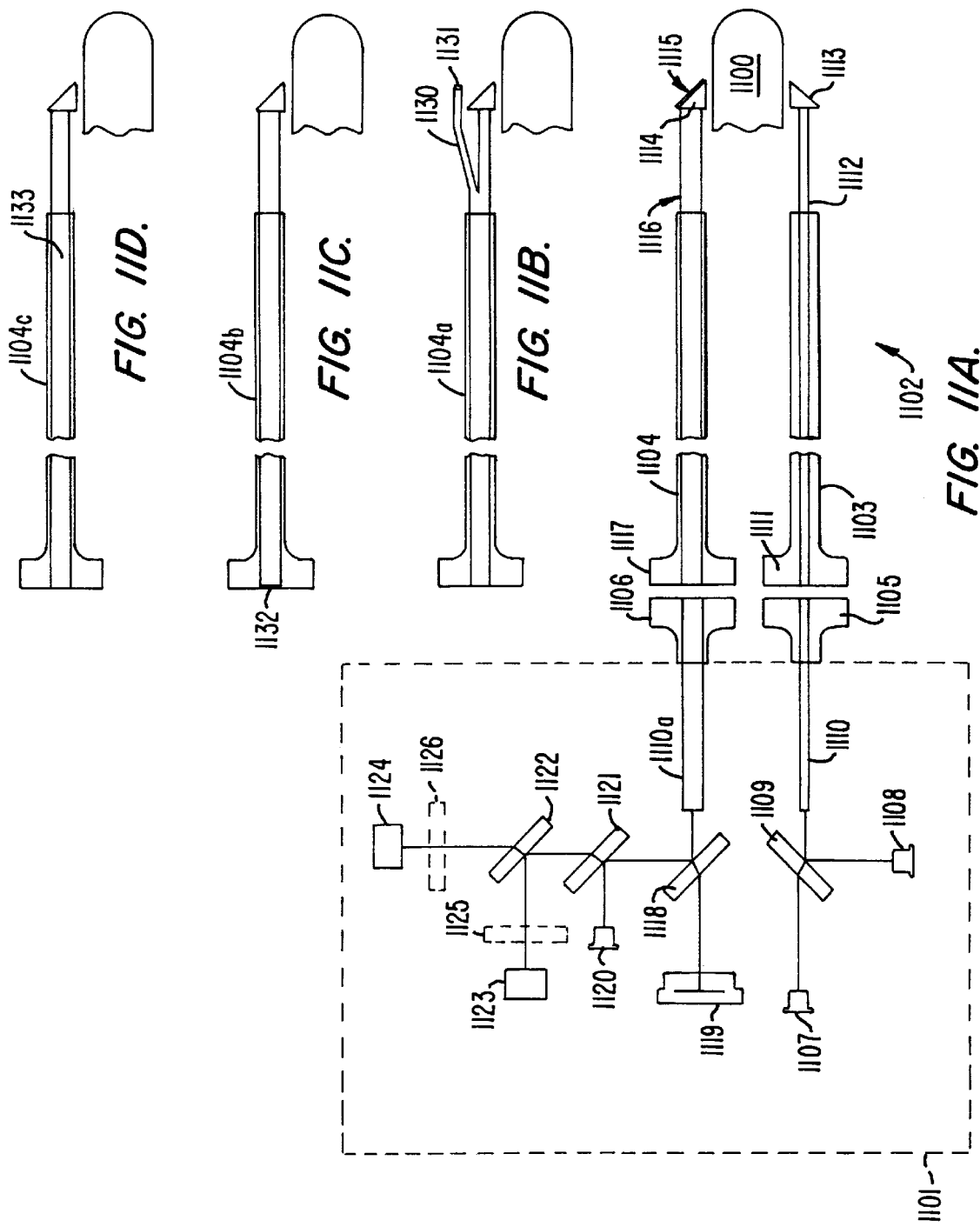

FIBER OPTIC OXIMETER CONNECTOR WITH ELEMENT INDICATING WAVELENGTH SHIFT

BACKGROUND OF THE INVENTION

The present invention relates to a fiber-optic pulse oximeter. More specifically, the present invention relates to a device for measuring and compensating for the wavelength shift of an optical signal.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patent's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption.

For measuring blood oxygen levels, sensors have been provided with light sources and photodetectors that are adapted to operate at two different wavelengths in accordance with known techniques for measuring blood oxygen saturation.

The operation depends upon knowing the wavelength of the LEDs. Since the wavelength of LEDs actually manufactured can vary, a resistor ("Rcal") is placed in the sensor with the value of the resistor corresponding to the actual wavelength of at least one of the LEDs. When the instrument is turned on, it first applies a current to the coding resistor and measures the voltage to determine the value of the resistor and thus the value of the wavelength of the LED in the probe. An example of such an encoding mechanism is shown in U.S. Pat. No. 4,700,708.

Another method of storing coded information regarding the characteristics of the LEDs is shown in U.S.

U.S. Pat. No. 4,942,877. This patent discloses using an EPROM memory to store digital information, which can be provided in parallel or serially from the sensor probe to the remote oximeter.

Other examples of coding sensor characteristics exist in other areas. In U.S. Pat. No. 4,446,715, assigned to Camino Laboratories, Inc., a number of resistors are used to provide coded information regarding the characteristics of a pressure transducer. U.S. Pat. No. 3,790,910 discloses another pressure transducer with a ROM storing characteristics of the individual transducer. U.S. Pat. No. 4,303,984 shows another sensor with digital characterization information stored in a PROM, which is read serially using a shift register.

Typically, the coding element is mounted in the sensor itself. For instance, U.S. Pat. No. 4,621,643 shows the coding resistor mounted in the sensor element itself. In addition, U.S. Pat. No. 5,246,003 shows the coding resistor being formed with a printed conductive material on the sensor itself.

In some devices, an electrical connector coupled by a cable to a device attached to a patient may include a coding element. For example, U.S. Pat. No. 3,720,199 shows an intra-aortic balloon catheter with a connector between the catheter and the console. The connector includes a resistor with a value chosen to reflect the volumetric displacement of the particular balloon. U.S. Pat. No. 4,684,245 discloses a fiberoptic catheter with a module between the fiberoptic and electrical wires connected to a processor. The module converts the light signals into electrical signals, and includes a memory storing calibration signals so the module and catheter can be disconnected from the processor and used with a different processor without requiring a recalibration.

In some applications, fiber optics have been used to carry the light from a remote light emitter and detector to a sensor probe attached to a patient. One such application is fetal oximetry, where it may be desirable to avoid electrical wires extending into the uterus. Another application would be for attaching to a patient undergoing an MRI examination, where there would be undesirable coupling between the MRI waves and the electrical cables. Examples of patents describing oximeters using fiber optics are U.S. Pat. No. 5,279,295, which shows a fiber-optic coupled pulse oximeter for an MRI environment, U.S. Pat. No. 5,096,294, which shows a DC oximeter for plants and U.S. Pat. No. 3,847,483.

Typically, a fiber optic can either be made of glass or plastic. Plastic fiber optics are typically cheaper, and easier to bend as needed. However, infrared light can have its wavelength significantly shifted over a length of plastic fiber optic cable, and to a lesser extent in glass cable. Since blood oxygen saturation calculations depend upon the infrared wavelength used, a shift can cause errors in the blood oxygen saturation calculation.

SUMMARY OF THE INVENTION

The present invention provides an oximeter probe segment with a first fiber optic for carrying light to a patient, and a second fiber optic for carrying return light from the patient. The light is of a wavelength spectrum which can be shifted by travelling through the first and second fiber optics. The probe segment includes an element which is configured to provide a signal corresponding to the shift of the wavelength spectrum through the first and second fiber optics. This signal can be used to actually measure the shift, or alternately the signal can itself be a coded value corresponding to the shift.

An oximeter can then use the signal corresponding to the shift to select or compute the appropriate coefficients to calculate blood oxygen saturation. The probe segment can either be connected to the sensor which attaches to a patient, or can be an intermediate adapter connected between the sensor and the oximeter.

In one embodiment, one or more separate fiber optic channels are provided as part of the element providing the shift signal. This separate channel(s) can either be used to directly measure the wavelength shift, or can provide a filtered or otherwise modified light signal corresponding to an encoding of the wavelength shift. Alternately, a resistor or other electrical impedance could be used to provide an encoding of the shift value.

In one embodiment, multiple probe segments are used, each with its own shift element corresponding to the wavelength shift through the particular segment. When the multiple segments are connected together, the signals from the shift elements combine to give a signal corresponding to the total combined shift. This allows convenient intermixing of adapter and extension cables in the field without the need for any particular matching.

For a fuller understanding of the nature and advantages of the invention, reference should be made to the ensuing detailed description taken in conjunction with the accompanying drawings.

BRIEF DESCRIPTION OF THE DRAWINGS

FIGS. 11A–11D are schematic diagrams illustrating a fiber optic system in which wavelength shift is encoded by provision of controlled amounts of fluorescent materials.

DETAILED DESCRIPTION

Figure 1:
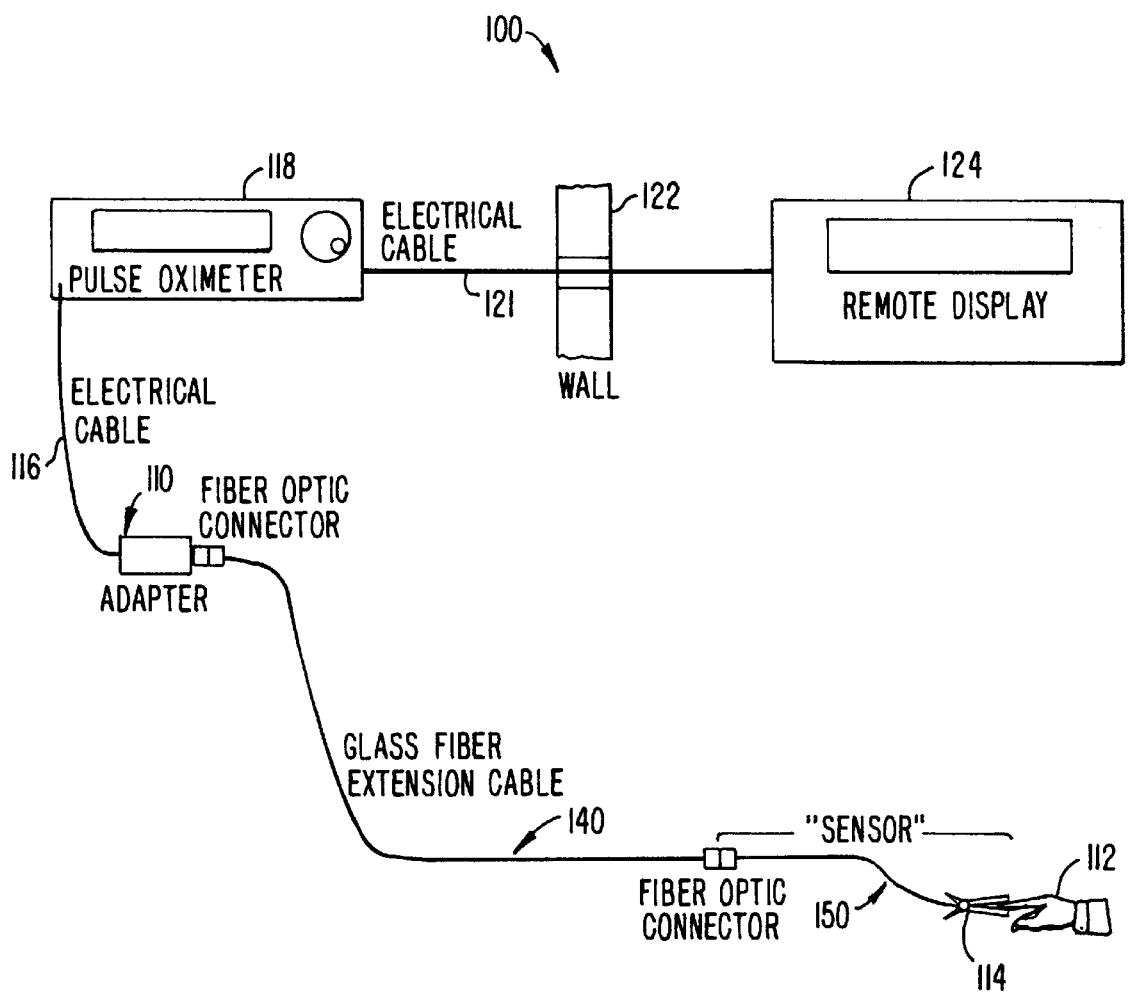
FIG. 1 is a diagram of a fiber-coupled pulse oximeter system.

An example of a fiber-coupled pulse oximeter system 100 is shown in FIG. 1. This particular system, for example, may be suitable for use in an MRI environment, and includes an adapter module 110 in which are located an emitter 120 and a detector 720 (as shown in the adapter embodiment of FIG. 7), along with suitable optics to couple these electro-optical components to the fiber optic bundles that guide light to and from the patient. There are two fiber optic cables in series—a long glass extension cable 140, which might be 15 feet long, and a relatively short "sensor" cable 150, which might contain either glass fibers or plastic fibers, that connects directly to the patient 112 via a sensor probe 114.

Adapter 110 is connected by an electrical cable 116 to a pulse oximeter 118. An example of an oximeter 118 is shown in more detail in FIG. 8. Oximeter 118 is connected by a separate electrical cable 121 through a wall 122 to an isolated, remote display 124. Wall 122 can isolate the display from the MRI radiation.

Typically, the pulse oximeter will employ light in two different spectral bands, one red and one infrared. The red light is typically not shifted much by travel through the fiber, but infrared light is significantly shifted, especially if the fiber is made of plastic. The shift typically occurs because the longer wavelengths that make up the band of light are absorbed more strongly by the fiber than are the shorter wavelengths, causing a shift in the mean wavelength of the light that remains after traveling through the fiber.

Figure 2A:
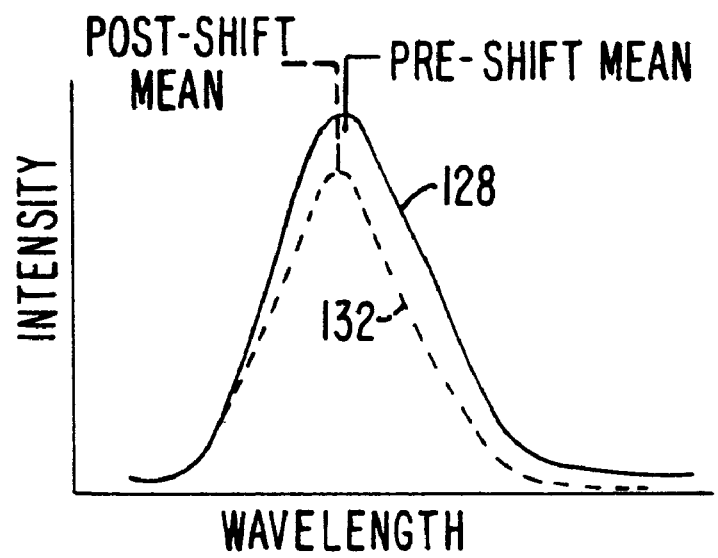
FIGS. 2A and 2B are graphs illustrating the effect of wavelength-dependent spectral absorption on mean wavelength.
Figure 2B:
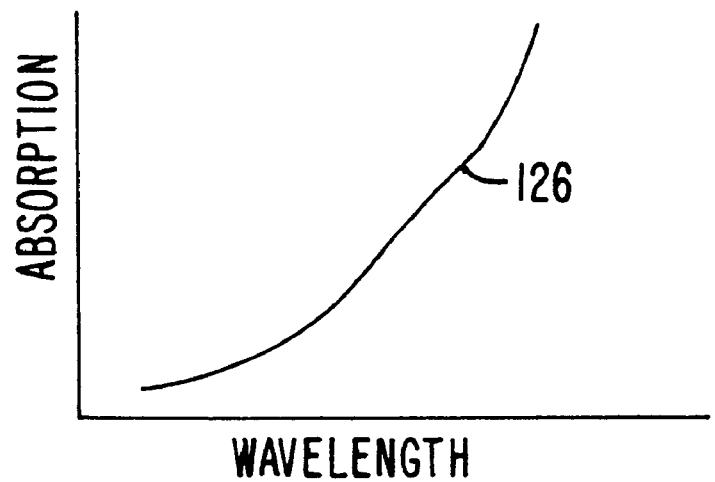

An example of the shifting phenomenon is shown schematically in FIGS. 2A and 2B. The wavelength-dependent absorption curve 126 shown in FIG. 2B causes the spectrum shown by the solid line 128 in FIG. 2A to become the spectrum shown by the dotted line 132 in FIG. 2A, with an associated shift in mean wavelength.

If all fiber optic sensors were to exhibit identical wavelength shift, it would be possible to deal with the shift in a particularly simple manner. The adapter module 110 shown in FIG. 1 would contain an Rcal resistor or other encoding means to indicate to the oximeter which of several stored calibration curves to use. The selected curve would be the correct one for the effective LED wavelengths resulting from the actual mean wavelengths of the LEDs in the adapter module, as shifted by the associated optical fibers. It is likely, however, that several variations of wavelength shift will be observed. For example, there might be several different lengths of plastic-fiber sensor cables or several different lengths of glass-fiber extension cable. Additionally, there might well be a variant in which the functions of sensor 150 and extension cable 140 were combined in a single glass or plastic fiber cable.

Figure 3:
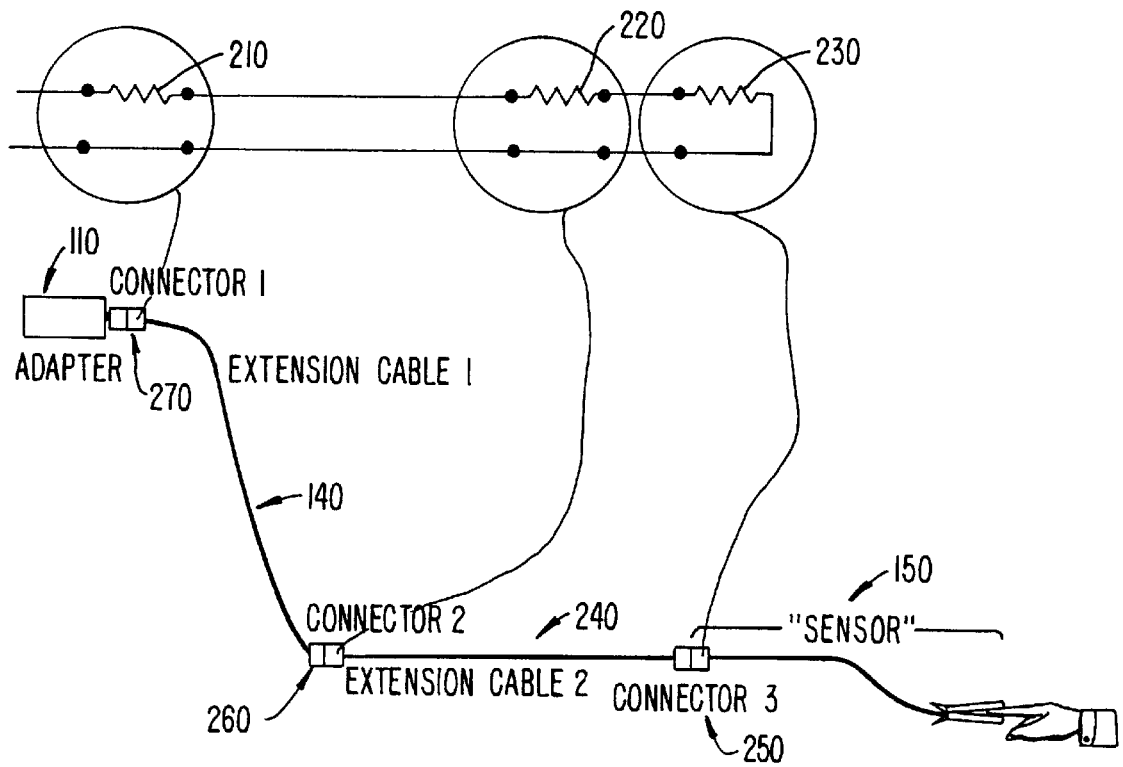
FIG. 3 is a diagram illustrating one way in which each element of a fiber optic string can report its wavelength shift contribution to an adapter module.

In one embodiment, each element of the fiber optic chain has a coding element to indicate to the adapter module what shift is produced by that element. An example is shown in FIG. 3. The sensor cable 150, which is to be connected to the patient, contains a coding resistor, 230, across two electrical pins which are included in the connector 250. No electrical wires are needed in sensor cable 150 which goes from connector 250 to the patient (this is desirable in an MRI environment, to avoid risk of burning the patient). Electrical wires are included along with the fiber optic bundles in the two extension cables (140 and 240) so that each of them can incorporate an appropriate coding resistor (210 and 220) in series with Resistor 230.

In FIG. 3, each coding resistor (210, 220, and 230) may have a resistance directly indicative of the wavelength shift produced by the associated optical fiber component so that the total series resistance is indicative of the total shift. Alternatively, the resistors may utilize "orthogonal" codes, so that it is possible for the adapter or the associated oximeter to determine separately the nature of each component of the string. For example, Extension cable 140 might utilize resistance values selected from 1000, 2000, 3000, . . . , 9000 ohms, Extension cable 240 might utilize values selected from 100, 200, 300, . . . , 900 ohms, and the sensor 150 might utilize values selected from 10, 20, 30, . . . , 90 ohms.

Figure 3A:
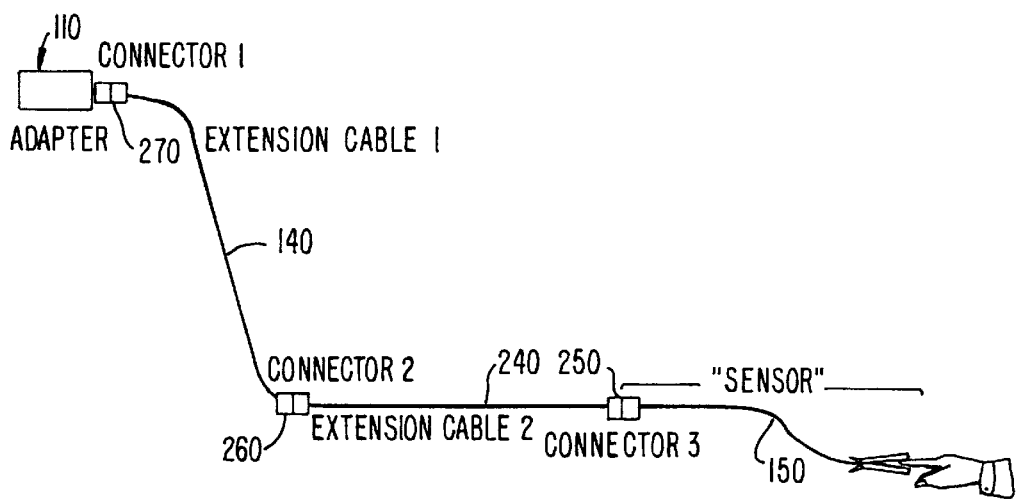
FIG. 3A is a diagram illustrating a fiber optic system using unique connectors to obtain the wavelength shift.

It is also possible to have versions of this invention in which there is no need for any electrical wires in any of the fiber optic cables. Such a system is shown in FIG. 3A. The simplest system to manufacture would use a single coding (Rcal) resistor or other coding element in the connector 270 of the cable that plugs directly into adapter 110. A system of unique connectors (250 and 260) would then be used to ensure that this cable could only be used with a total system having a corresponding particular value of wavelength shift. Thus, if two different sensor cables, having different wavelength shifts, were to be used, each would have a unique corresponding extension cable, and incompatible connectors would prevent a mismatch of sensor and extension cable.

Figure 3B:
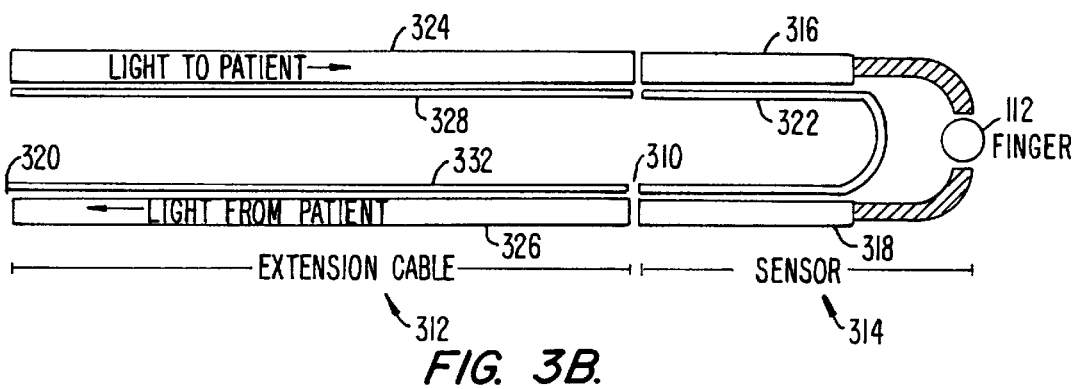
FIG. 3B is a diagram illustrating an all optical system for indicating wavelength shift in a number of fiber optic elements.

An all-optical means of conveying information about a cable string including sensor and in-line extension cables to the adapter to which the string is connected is shown in FIG. 3B. FIG. 3B shows an extension cable element 312 and a sensor element 314. Sensor element 314 includes first and second fiber optics 316 and 318 for directing light to and from patient 112. In addition, a separate fiber optic 322 provides encoding information, which is accomplished by selecting a particular value for a filter 310.

Extension 312 includes fiber optic elements 324 and 326 for connecting to elements 316 and 318, respectively, of sensor element 314. In addition, separate fiber optics 328 and 332 are provided to connect to element 322 of sensor element 314. A second filter 320 encodes the amount of wavelength shift along fiber optics 324 and 326. The two filters will provide a combined filtering corresponding to the combined shift through elements 312 and 314. Thus, in place of coding resistors, the connectors contain optical filters (310 and 320) whose transmission would encode information. A particularly useful variant encodes the information as the ratio of filter transmissions at two different wavelengths. This supports measurement by a method independent of the strength of an emitting source.

Figure 4:
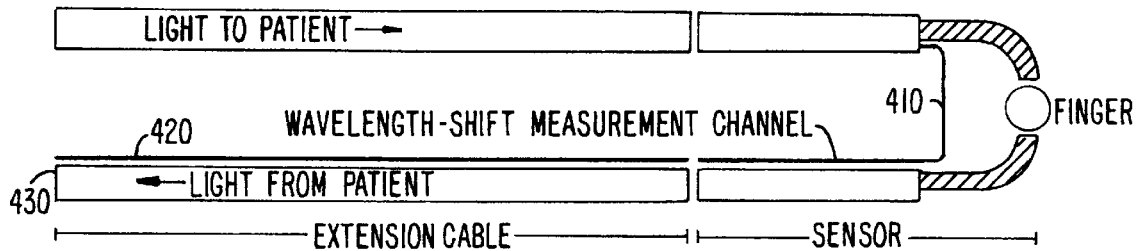
FIG. 4 is a diagram illustrating a fiber-optic system containing a wavelength-shift measurement channel.

Another useful variation forgoes coding but instead facilitates direct measurement of the wavelength shift induced by a cable string. This approach is illustrated in FIG. 4. It may use the same pair of light sources that are employed for pulse oximetry. A few of the fibers 410 that arrive at the sensor are looped back and fed into a separate channel 420 back to the adapter so that the adapter receives two separate signal channels, one (430) of which represents light that has been through both fiber and patient and the other (420) of which has been only through fiber. Wavelength shift of the fiber-only channel may be measured, for example, by comparing the intensity of transmission through two different optical filters, one of which transmits more strongly in the upper half of the LED emission band and one which transmits more strongly in the lower half, as described in more detail below and in FIGS. 9–10.

Figure 5:
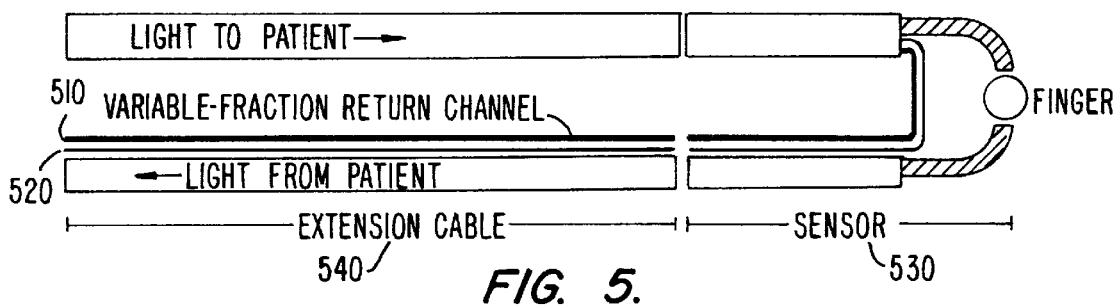
FIG. 5 is a diagram illustrating a fiber-optic system with two fiber optic code-return channels.
Figure 6:
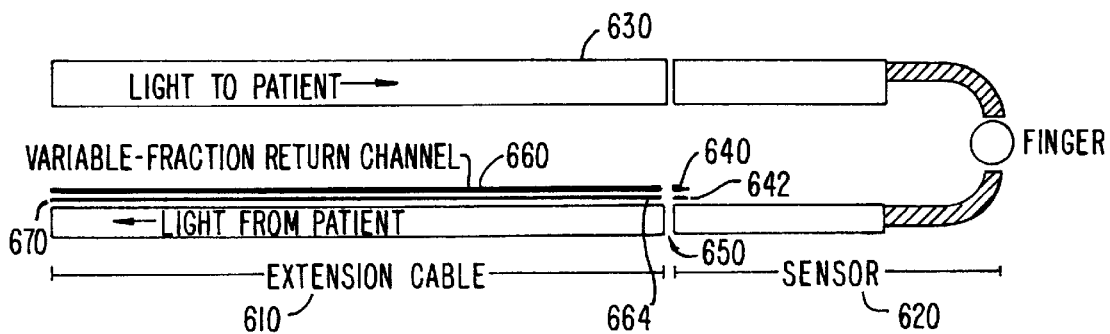
FIG. 6 is a diagram illustrating a fiber-optic system with two fiber optic return channels.

Returning now to the general approach of encoding wavelength-shift information rather than measuring the actual shift while the sensor is in use, FIGS. 5 and 6 illustrate two other variations. FIG. 5 shows a system in which encoded information is represented by the ratio of optical power flowing in two auxiliary optical fiber channels (510 and 520). With this setup, in addition to the main signal channel that returns light that has passed through the patient's tissue, there are two extra channels. The fixed channel 520 carries a constant fraction of incident light and the variable channel 510 carries an amount that differs for each different type of sensor 530 that may be connected to the extension cable 540. The ratio of the amount of light returned by the two extra channels conveys information about the wavelength shift contributed by the particular type of sensor that is connected. In the variant shown here, the amount of returning light may be set by diverting some number of the plastic fibers in the bundle that arrives at the patient's finger. In another variant, the amount of light returned through the variable channel 510 might be set by choice of a simple molded plastic optical channel built into the connector of the sensor.

Implicit in the particular form shown in FIG. 5 is that the code-carrying fibers are plastic (for best economics), that the source light is simply a small portion of the same light which is delivered to the sensor for oximetry measurements, and that the long section of plastic fiber in the extension cable attenuates the infrared portion of the light to the point of negligibility. Therefore, the encoding information is carried by the red light delivered to the oximeter without compli- cating effects caused by the infrared light also delivered. If there is any possibility of interfering effects caused by remaining infrared light, this light can be eliminated with a simple optical filter. As described above, the principle of operation in FIG. 5 is that one of the fiber return channels 520 carries a constant proportion of the light delivered to the sensor (e.g., the light which is carried to the sensor by one 0.25 mm diameter plastic fiber selected from the bundle of such fibers that arrives at the end of the sensor proximal to the patient's finger) and that the other fiber return channel 510 returns a proportion of the delivered light chosen to encode information about the amount of wavelength shift caused by the sensor. Also implicit is that, in :he particular variant illustrated, there is no contribution to wavelength shift from the extension cable 540. If, in fact, the extension cable 540 does make a contribution Go wavelength shift, then optical components must be added to each extension cable so that the power ratio of the returning pair of signals will be altered by the extension cable.

A second alternative system to FIG. 5 is illustrated in FIG. 6. In this system variant, illumination comes up the same channels (660, 664) through which it returns by virtue of reflectors 640, 642, respectively. The reflectors 640 may be no more complex than pieces of shiny aluminum. Illumination might be provided by the same light sources that illuminate the patient-signal channel or might be provided by a separate lamp, such as an LED. If a broadband source, such as an incandescent lamp, were used for the two code channels, it would create the option of encoding additional information through use of color selective reflectors. Consequently, in other words, rather than the two channels being illuminated by using light "stolen" from main channel 630 that sends light through the patient, the light to be used for encoding is sent upstream toward the sensor in the same optical channels through which it returns from the sensor 620. A reflector 640 built into the connector 650 of the sensor 620 determines what fraction of incident light 670 returns through the variable channel 660. The ratio of the light reflected in variable channel 660 to the light reflected in fixed channel 664 is an encoded value of the wavelength shift.

FIG. 11A is a schematic diagram of another alternative system which encodes wavelength shift. In this system, the encoding means is a fluorescent element containing two different fluorophores, which are stimulated by a single wavelength band of stimulating radiation to emit light in two different wavelength bands. By selecting the relative amounts of the two fluorophores, it is possible to encode information as to the wavelength shift induced by a particular model of sensor. An advantage of this construction is that, in some of its forms, no additional fiber optic elements are needed, beyond those which would be required to conduct oximetry.

FIG. 11A shows pulse oximeter sensor 1101, within which have been illustrated only those optical components essential to a description of this invention. Instrument 1101 delivers light to the afferent portion 1103 of a fiber optic assembly 1102, which delivers light to patient tissue 1100. Light having passed through tissue 1100 is returned by efferent portion 1104 of assembly 1102 to oximeter 1101.

Considering the optical path in more detail, we see that light is emitted by red LED 1107 and infrared LED 1108, combined by dichroic beamsplitter 1109, and delivered to fiber optic segment 1110 (auxiliary optics required for efficient coupled are not shown). Fiber segment 1110 terminates in outgoing connector 1105, which mates to connector 1111 of assembly 1102. Light travels through fiber optic 1112 to optics 1113 which direct the light into patient tissue 1100. Optics 1113 are shown as a simple prism, although other optical coupling means are possible. Upon exiting from tissue 1100, light is collected and redirected into fiber 1116 by optical element 1114, here shown as a prism. Coated onto a surface of element 1114 is a patch 1115 of fluorescent chemicals, which are so positioned as to be able to interact with evanescent waves produced by light passing through element 1114 and contacting the surface on which patch 1115 resides. The light is conducted through mating connectors 1117 and 1106 into fiber segment 1110a, and thence through dichroic beamsplitter 1118 to oximetry detector 1119. The coatings on beamsplitter 1118 are selected to transmit both the red and the infrared spectral bands used in oximetry, but to reflect shorter wavelengths. Thus, oximetry can proceed essentially as it would in the absence of the fluorescent encoding means.

Now consider the elements which contribute to determination of the code carried by fluorescent patch 1115. LED 1120 emits fluorescence-stimulating light, which may be blue. This light reflects from beamsplitters 1121 and 1118 to enter fiber segment 1110a, then travels in reverse along efferent channel 1104 until it strikes fluorescent patch 1115 and stimulates the emission of two bands of fluorescent light. A portion of this fluorescent light is conducted back to the instrument via channel 1104, reflects from beamsplitter 1118, and is transmitted through beamsplitter 1121. This light is then divided into its two different color bands by dichroic beamsplitter 1122, and the two bands are detected by detectors 1123 and 1124. Optionally there may be supplementary wavelength-selective filters 1125 and 1126, to purify the spectral bands of light seen by each of detectors 1123 and 1124.

Also shown in FIGS. 11B–11C are three alternate forms of the efferent fiber assembly, which may be substituted for assembly 1104, to illustrate some of the other possible ways of implementing fluorescent encoding.

Assembly 1104a of FIG. 11B has at its patientconnected end a separated subgroup 1130 of the fibers which make up the fiber optic cable. Fluorescent patch 1131 is applied to an end of this subgroup of fibers.

Assembly 1104b of FIG. 11C has fluorescent patch 1132 applied to the end of the fiber optic which mates with instrument connector 1106.

Assembly 1104c of FIG. 11D comprises optical fibers which have been doped with fluorescent material, so that, upon appropriate stimulation, fluorescent light is emitted by the bulk fiber. In one implementation, fiber bundle 1133 would comprise two types of doped fibers, which had been doped with two different types of fluorescent material, emitting at different wavelengths. By choosing the proportion of the two types of fibers included in bundle 1133, it would be possible to select a particular ratio of intensities of the two emission wavelengths.

Figure 7:
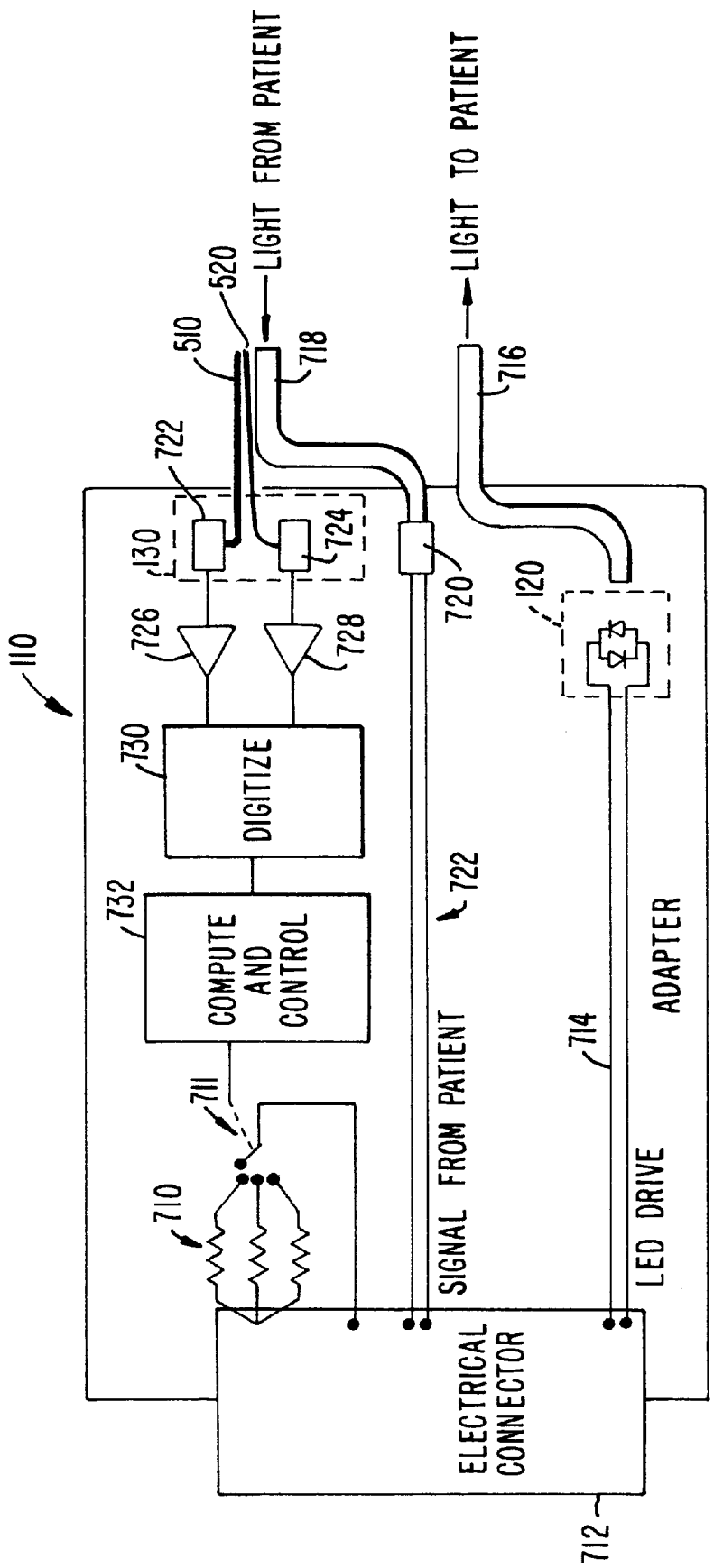
FIG. 7 is a diagram illustrating the adapter module of FIG. 1 for use with a two-channel wavelength-shift encoding scheme.

FIG. 7 is a schematic diagram of adapter module 110 of FIG. 1 configured to deal with wavelength-shift information coming back from the sensor. Adapter 110 is shown for working with the configuration of FIG. 5. An electrical connector 712 connects to a cable 116 as shown in FIG. 1 and to the pulse oximeter 118. Connector 712 includes wires 714 which drive an emitter 120, including a red and infrared LED. The light is provided over a fiber optic cable 716, with the light returning from the patient being provided on a return fiber optic 718 to a detector 720. Detector 720 provides its signal over wires 722 to connector 712 for transmission to pulse oximeter 118.

Variable and fixed fraction return channels 510 and 520 are connected to a detector 130 including photodetectors 722 and 724. These are connected to amplifiers 726 and 728, respectively. The amplified signals are then digitized in an analog-to-digital converter 730, and provided to a computation and control circuit 732. The computation circuit 732 determines the ratio of light returning in the two coding channels 510 and 520. Based on this ratio, it decides which of several Rcal resistors 710 should be selected by switch 711 so as to communicate to the oximeter instrument which of several alternative calibration curves should be used.

Figure 8:
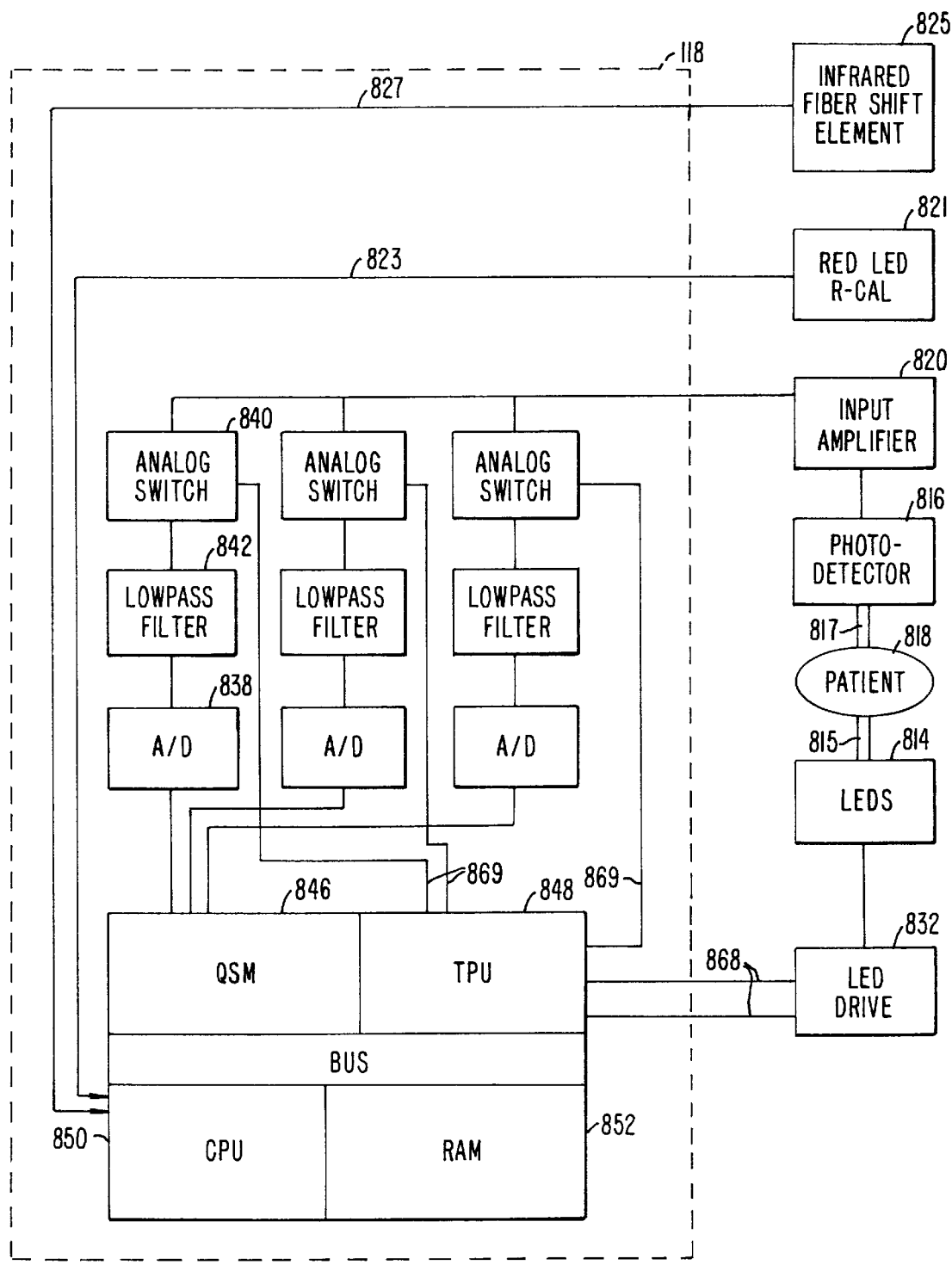
FIG. 8 is a block diagram of an oximeter monitor.

FIG. 8 is a block diagram of one embodiment of a pulse oximeter 118. Light from LEDs 814 passes through fiber optics 815 into patient tissue 818, and after being transmitted through or reflected from tissue 818, the light is received by photosensor 816 through fiber optics 817. Either two or three LEDs can be used depending upon the embodiment of the present invention. Photosensor 816 converts the received energy into an electrical signal, which is then fed to input amplifier 820.

Light sources other than LEDs can be used. For example, lasers could used, or a white light source could be used with appropriate filters either at the transmitting or receiving ends.

Time Processing Unit (TPU) 848 sends control signals 868 to the LED drive 832, to alternately activate the LEDs. Again, depending on the embodiment, the drive may control two or three LEDs.

The signal received from input amplifier 820 is passed through three different channels as shown in the embodiment of FIG. 8, for three different wavelengths. Alternately, two channels for two wavelengths could be used. Each channel includes an analog switch 840, a low pass filter 842, and an analog to digital (A/D) converter 838. Control lines 869 from TPU 848 select the appropriate channel at the time the corresponding LED 814 is being driven, in synchronization. A queued serial module (QSM) 846 receives the digital data from each of the channels. CPU 850 transfers the data from QSM 846 into RAM 852 as QSM 846 periodically fills up. In one embodiment, QSM 846, TPU 848, CPU 850 and RAM 852 are part of one integrated circuit, such as a DMC68HC16 microcontroller from Motorola.

A resistor or other impedance or active element 821 provides a signal on line 823 to CPU 850 corresponding to the wavelength of the red LED of LEDs 814, as known in the prior art. The present invention adds an infrared fiber shift element 825 which provides a signal over line 827 to CPU 850. As explained elsewhere herein, element 825 either encodes the infrared wavelength shift through fiber optics 815, 817, or enables the measurement of the shift. This could be done with an encoding resistor, a separate fiber optic and a filter, or by a number of other mechanisms.

Figure 9:
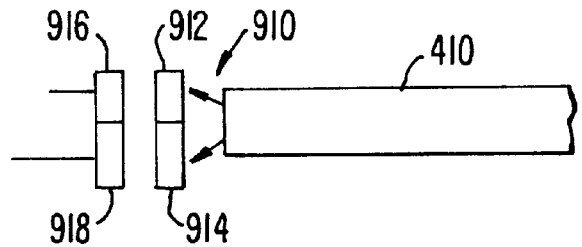
FIG. 9 is a diagram of an embodiment of an optical shift measuring element.

FIG. 9 illustrates an element for measuring the wavelength shift. A return fiber optic 410, such as shown in FIG. 4, could be used to provide return light 910 which is provided through separate filters 912 and 914. The filtered signals are detected by respective detectors 916 and 918.

Figure 10A:
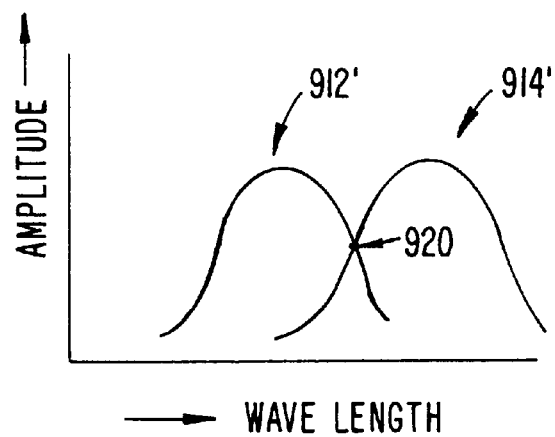
FIGS. 10A and 10B are graphs illustrating optical shift measurement using filters and reflectors.

FIG. 10A illustrates a filter response for one example of filters 912 and 914, with the responses indicated as 912' and 914'. As should be apparent, if these two separate filters are used, and would normally have equal intensities for a centered emitted signal, the shift can be detected by measuring the ratio or difference of intensities. A shift to a shorter wavelength would provide more light through filter 912, and less through 914, and vice versa. Preferably, the filters are chosen such that a mid-point 920 has approximately 50% transmission through both filters.

Figure 10B:
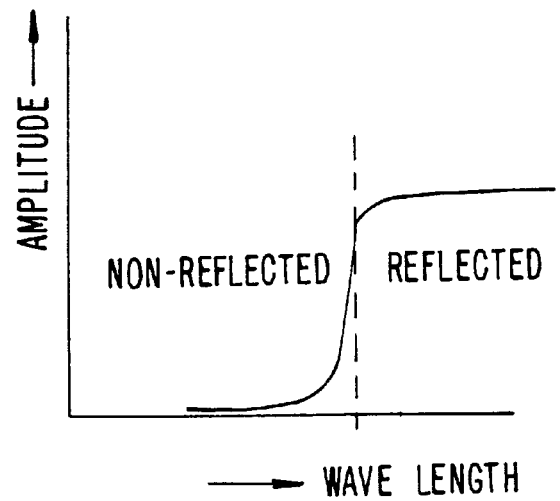

An alternate embodiment is illustrated in FIG. 10B also for measuring, as opposed to encoding, the wavelength shift in a reflective system. An example of a reflective system is shown in FIG. 6. A first channel 664 and fixed reflector 642 provide reflected light showing a control intensity reflected back. Variable reflector 640, instead of encoding a value, is simply a reflector with a variable reflectance depending on the wavelength, as illustrated in FIG. 10B. In the example shown, lower wavelengths would be absorbed and not reflected very much, while higher wavelengths would be reflected. Thus, if the midpoint is correctly chosen, the amount of wavelength shift into the nonreflective portion will reduce the intensity of the reflected signal compared to the intensity of the control signal. By measuring the decrease in intensity, the amount of wavelength shift can be determined. The resulting differential could be multiplied by 2 to account for the fact that the reflection occurs only after travelling up the fiber optic, and doesn't incorporate shift on the return path. The embodiment of FIG. 6 will only show the shift for the segment up to the reflector. The reflector could alternately be placed closer to the sensor to give an approximation of the total shift.

As will be understood by those of skill in the art, the present invention may be embodied in other specific forms without departing from the spirit or essential characteristics thereof. For example, the coding could be placed in a connector as a mechanical element which trips one or more switches in a mating connector, or which can be read by an optical element in one connector. It will also be recognized by those skilled in the art that, while specific embodiments have been described herein that apply to pulse oximetry, this invention will actually be useful in any fiber-coupled optical medical sensing system, for measuring a biological analyte, in which system the wavelength shift of light going through an optical fiber would be a potential source of error if the measuring instrument were not aware of the amount of induced shift. Accordingly, the foregoing description is intended to be illustrative, but not limiting, of the scope of the invention which is set forth in the following claims.

What is claimed is:

1. A probe segment for use in an optical medical sensing system comprising:

a first fiber optic configured to carry a first wavelength spectrum of light to be directed to a patient;

a second fiber optic configured to carry light of said first wavelength spectrum from said patient; and an element configured to provide a signal corresponding to a wavelength shift of said first wavelength spectrum through said first and second fiber optics.

2. The probe segment of claim 1 wherein said element is configured to enable a measurement of said wavelenght shift of said first wavelength spectrum.

3. The probe segment of claim 1 wherein said element is configured to provide a coded value corresponding to said wavelenght shift of said first wavelength spectrum.

4. The probe segment of claim 1 wherein said first wavelength spectrum is an infrared spectrum.

5. The probe segment of claim 1 wherein said first wavelength spectrum is an infrared spectrum, and further comprising:

a red wavelength spectrum emitter coupled to said first fiber optic; and a second element configured to provide a signal corresponding to said second, red wavelength spectrum.

6. The probe segment of claim 1 wherein said probe segment comprises first and second connectable segments, said first and second fiber optics and said element being mounted in said first connectable segment, said second connectable segment comprising:

a third fiber optic connected to said first fiber optic;

a fourth fiber optic connected to said second fiber optic; and a second element configured to provide a signal corresponding to a wavelength shift of said first wavelength spectrum through said third and fourth fiber optics.

7. The probe segment of claim 1 wherein said element comprises an electrical impedance.

8. The probe segment of claim 1 wherein said element comprises a separate, third fiber optic.

9. The probe segment of claim 8 wherein said element further comprises a fourth fiber optic, said fourth fiber optic being configured to carry a fraction of the light of said third fiber optic.

10. The probe segment of claim 8 wherein said third fiber optic is substantially the length of the combination of said first and second fiber optics.

11. The probe segment of claim 8 wherein said third fiber optic is substantially the length of one of said first and second fiber optics, and further comprising a reflector mounted at one end of said third fiber optic.

12. The probe segment of claim 8 wherein said element further comprises a filter coupled to said third fiber optic for encoding a value corresponding to said first wavelength spectrum.

13. The probe segment of claim 1, wherein said element comprises a first amount of a first fluorophore and a second amount of a second fluorophore, the ratio of said first amount to said second amount being selected to correspond to said wavelength shift.

14. The probe segment of claim 1 wherein said optical medical sensing system is an oximeter system.

15. An oximeter probe system comprising:

a red wavelength spectrum emitter;

an infrared wavelength spectrum emitter;

at least one fiber optic coupled to said red and infrared wavelength spectrum emitters;

a first element configured to provide a coded value corresponding to a wavelength shift of said infrared wavelength spectrum through said fiber optic; and a second element configured to provide a signal corresponding to said red wavelength spectrum.

16. An oximeter probe system comprising:

a first emitter, for emitting red light;

a second emitter, for emitting infrared light;

a third emitter, for emitting light of a fluorescence-stimulating wavelength;

at least one fiber optic coupled to said first, second, and third emitters; and an element configured to provide a coded value corresponding to a spectral shift of said infrared light when transmitted through said fiber optic, wherein said element comprises a first amount of a first fluorophore and a second amount of a second fluorophore, said fluorophores being responsive to said fluorescence-stimulating wavelength, the ratio of said first amount to said second amount being selected to correspond to said spectral shift.

17. A probe system for optical medical sensing comprising:
- a first segment including
    - a first fiber optic configured to carry a first wavelength spectrum of light to be directed to a patient,
    - a second fiber optic configured to carry light of said first wavelength spectrum from said patient, and
    - an element configured to provide a first signal corresponding to a shift of said first wavelength spectrum through said first and second fiber optics; and
- a second segment, connected to said first segment, said second segment including
    - a third fiber optic connected to said first fiber optic,
    - a fourth fiber optic connected to said second fiber optic, and
    - a second element configured to modify said first signal to provide a combined signal including information corresponding to a wavelength shift of said first wavelength spectrum through said third and fourth fiber optics.

18. An optical medical sensing instrument for use with a probe segment having first and second fiber optics said instrument comprising:
- a processor configured to operate on a second signal corresponding to an amount of light received through said second fiber optic, using appropriate coefficients, for determining the concentration of a biological analyte; and
- a decoder, responsive to a first signal from an element in said probe segment corresponding to a wavelength shift of a first wavelength spectrum through said first and second fiber optics, to select said appropriate coefficients.

19. The instrument of claim 18 further comprising a table of said coefficients coupled to said decoder.

20. The instrument of claim 18 wherein said processor computes said coefficients.

* * * * *